United States Patent [19]

Albers et al.

[11] Patent Number: 5,449,655
[45] Date of Patent: Sep. 12, 1995

[54] PROCESS FOR PREPARING HYDROGENATION CATALYSTS WHICH CONTAIN NOBLE METALS ON ACTIVATED CARBON

[75] Inventors: Peter Albers; Roland Burmeister, both of Hanau; Klaus Deller, Hainburg, all of Germany; Bertrand Despeyroux, Fourqueux, France

[73] Assignee: Degussa Aktiengesellschaft, Frankfurt am Main, Germany

[21] Appl. No.: 212,725

[22] Filed: Mar. 14, 1994

[30] Foreign Application Priority Data

Mar. 15, 1993 [DE] Germany ............... 43 08 101.0

[51] Int. Cl.$^6$ .................. B01J 23/38; B01J 21/18
[52] U.S. Cl. .......................... 502/185; 502/182
[58] Field of Search .................. 502/182, 185

[56] References Cited

U.S. PATENT DOCUMENTS

| 3,138,560 | 6/1964 | Keith et al. | 252/447 |
| 3,150,185 | 9/1964 | Luvisi et al. | 260/576 |
| 4,111,842 | 9/1978 | van Montfoort et al. | 252/447 |
| 5,132,452 | 7/1992 | Deller et al. | 562/531 |
| 5,302,765 | 4/1994 | Manzer et al. | 570/123 |

FOREIGN PATENT DOCUMENTS

| 0418573 | 3/1991 | European Pat. Off. . |
| 0573910 | 12/1993 | European Pat. Off. . |
| 2042368 | 4/1971 | Germany . |
| 2150220 | 4/1973 | Germany . |
| 3119707 | 12/1982 | Germany . |
| 4218866 | 1/1994 | Germany . |

OTHER PUBLICATIONS

1987 Elsevier Science Publishers, Preparation of Highly Dispersed, Carbon Supported, Platinum Catalyst, Richard et al. pp.71–79.
Ullmann's Encyclopedia of Industrial Chemistry, 1985, vol. A5, pp. 124–140.

*Primary Examiner*—Sharon A. Gibson
*Assistant Examiner*—Timothy H. Meeks
*Attorney, Agent, or Firm*—Beveridge, DeGrandi, Weilacher & Young

[57] ABSTRACT

A process is described for preparing hydrogenation catalysts which contain noble metals, having at least one catalytically active component and optionally promoters and/or modifiers on a support consisting of activated carbon washed with nitric acid. The activated carbon is subjected to an oxidative pretreatment with an oxidizing agent before applying the catalytically active components, promoters and modifiers.

7 Claims, No Drawings

PROCESS FOR PREPARING HYDROGENATION CATALYSTS WHICH CONTAIN NOBLE METALS ON ACTIVATED CARBON

INTRODUCTION AND BACKGROUND

The present invention relates to a process for preparing hydrogenation catalysts which contain noble metals and having at least one catalytically active component and optionally promoters and/or modifiers on a support of activated carbon.

The hydrogenation of organic compounds is performed on a large-scale in the presence of catalysts which contain noble metals on activated carbon. An important field of application is for example, hydrogenation of haloamines. The activity and selectivity of these catalysts may be influenced by promoters and modifiers. Promoters reinforce the catalytic effect whereas modifiers alter the selectivity by partially poisoning the catalyst. Depending on the reaction which is desired, specific components may act in one case as promoters and in another case as modifiers. According to German patent 21 50 220, U.S. Pat. No. 3,150,185, German OLS 20 42 368 and German patent application P 42 18 866.0-41 which has still not been laid open to public inspection, suitable noble metals are the metals Pt, Pd, Rh, Ru, Os and iridium. S, Pb, Bi, Ag, Cu and Fe may be used as modifiers.

The support used for these catalytically important components is preferably activated carbon in a finely divided form with an average particle diameter of 15 to 30 μm or as molded items with dimensions of 1 to 5 mm. A variety of such molded shapes such as pellets are known.

As is well known, activated carbon is a natural product and is obtained from carbon-containing materials by charring followed by chemical or gas activation. Suitable carbon-containing materials are various woods such as beech, pine or coconut shells (Ullmann's Encyclopedia of Industrial Chemistry, Weinheim 1985, vol. A5, pages 124–140).

Activated carbon is characterized by a particularly high specific surface area of 500–1500 $m^2/g$, which may be determined from nitrogen adsorption isotherms and assessment by the Brunauer, Emmett and Teller (BET) method (DIN 66132). The high specific surface area of activated carbon is based on the large pore volume of up to 1.5 ml/g, more than one third of which usually consists of micropores with pore diameters of less than 2 nm.

Commercial activated carbon has an ash content of up to 20%, which consists of inorganic components from the starting material. For catalytic applications, only activated carbons with the smallest possible ash contents may be used. This is usually achieved by washing the activated carbon with strong inorganic acids such as, for example, hydrochloric acid and nitric acid. These procedures are well known in the art.

In this way both the ash content of the activated carbon support is drastically reduced, especially by the removal of compounds which contain alkaline earth and heavy metals, and the surface of the support is freshly functionalised. These two properties, inter alia, have an advantageous effect on the final catalyst with regard to catalyst activity and product selectivity in the chemical reactions concerned. Typical residual ash contents are less than 2 wt. %.

Richard and Gallezot ("Preparation of highly dispersed carbon supported, platinum catalyst" Stud. Surf. Sci. Catal., 31 (Prep. Catal. 4), 71–81; 1987, Elsevier Science Publishers B.V. Amsterdam) investigated the functionalisation of surfaces of carbon supports using different oxidizing agents. They found that the surface could also be functionalised using sodium hypochlorite or hydrogen peroxide as an alternative to concentrated nitric acid (65%). The number of functional groups obtained, however, was much smaller when using hydrogen peroxide, even when applied in 30% strength aqueous solution for a period of 24 hours, than when using concentrated nitric acid.

To prepare hydrogenation catalysts, an initial activated carbon is used whose residual ash content has been reduced to less than 2 wt. % by washing with nitric acid. Suitable noble metals have to be deposited on this activated carbon. For this as is described, for example, in P 42 18 866.0-41, powdered activated carbon is suspended in water. After the addition of aqueous solutions of water-soluble compounds of noble metals and optionally of modifiers to the activated carbon suspension, noble metals and modifiers are precipitated onto the activated carbon in the form of their barely soluble compounds by the addition of a base to the suspension. Then follows reduction of the catalytically important components, using a reducing agent such as hydrazine, sodium formate, sodium borohydride or formaldehyde.

It has been shown that the hydrogenation catalysts prepared in this way have very large variations in hydrogenation activity and selectivity. This can be attributed to variations in the quality of these activated carbon supports which originate from natural sources.

In particular, the low ash contents and the functionalised surfaces cannot always be set by washing with nitric acid under economically viable, large-scale conditions.

There is generally an optimum for the washing conditions for a specific type of activated carbon. Experience has shown that the performance of the resulting catalysts is negatively affected by washing with too high concentrations of nitric acid and using too long washing times.

SUMMARY OF THE INVENTION

The object of the present invention is to provide a process for preparing hydrogenation catalysts on activated carbon supports which reduces the observed variations in catalytic activity and in addition provides catalysts which are more active.

This object is achieved by a process for preparing hydrogenation catalysts which contain noble metals having at least one catalytically active component and optionally promoters and/or modifiers on a support of activated carbon washed with nitric acid.

In achieving the above and other objects, one feature of the invention resides in the process wherein the activated carbon support is subjected to an oxidative pretreatment, using an oxidizing agent, before applying the catalytically active components, promoters and modifiers.

Noble metals from the platinum group or combinations thereof may be used as catalytically active components.

Hydrogen peroxide or sodium hypochlorite are suitable as an oxidizing agent, hydrogen peroxide being preferred.

DETAILED DESCRIPTION OF THE INVENTION

Surprisingly, it was found that variations in performance of the catalysts can be reduced by this type of oxidative pretreatment of the activated carbon already washed with nitric acid. In addition, the activity was increased as compared with conventionally prepared catalysts.

The oxidative pretreatment of activated carbon is preferably implemented in the form of washing with an aqueous solution which contains 0.1 to 30 percent by weight of hydrogen peroxide or sodium hypochlorite at room temperature for a period of 10 to 300 minutes.

In place of the hydrogen peroxide, a compound generating hydrogen peroxide can be used. Therefore, any suitable source of hydrogen peroxide can be used.

The invention is explained in more detail in the following, using a few examples. Two different production batches (batch 1 and batch 2) of a commercially available activated carbon made from beech wood with a BET surface area of ca. 900–1000 $m^2/g$, a total pore volume of 0.9–1.0 ml/g and an average particle size of 23 μm, washed with nitric acid, were used in the examples. The ash content of the activated carbon was less than 2%, i.e., below the level of detection with available equipment.

COMPARISON EXAMPLE 1

99.8 g of activated carbon (dry weight of batch 1) were impregnated with a 20 wt. % strength aqueous solution of tetrachloropalladic acid and heated to 80° C. Then the desired metallic phase was established by precipitation with a 10 wt. % strength aqueous solution of NaOH and reduction with formaldehyde at 80° C. Finally, the catalyst was filtered off and washed with water. The final catalyst contained 5 wt. % of palladium on activated carbon.

COMPARISONE EXAMPLE 2

A second catalyst was prepared in exactly the same way as in comparison example 1 using activated carbon from batch 2.

EXAMPLES 1 AND 2

130 g of the activated carbons cited in comparison examples 1 and 2 (dry weight) (batch 1 for examples 1 and batch 2 for example 2) were initially placed in 800 ml of $H_2O$. 50 ml of a 30% strength $H_2O_2$ solution were added to this suspension and stirred for 4 hours. After filtering off, the activated carbon was washed with water.

The catalysts were then prepared as described in the comparison examples.

Testing the catalysts

To measure catalytic performance, the catalyst activity was tested in the hydrogenation reaction of cinnamic acid to give dihydrocinnamic acid.

The catalyst activity was measured in milliliters of hydrogen consumed per gram of catalyst per minute (ml $H_2$/g catalyst.min). The reaction interval used for calculating this catalyst activity was the reaction time between the third and eighth minutes from the time the hydrogen was first introduced.

A reaction solution comprising 10 g of cinnamic acid and 200 mg of catalyst in a mixture of 80 ml of water and 40 ml of ethanol was initially introduced in a 250 ml stirred reactor with a blower-stirrer, thermometer and hydrogen feed. The hydrogen required for hydrogenation was distributed in the reaction solution at a reaction temperature of 25° C., an excess pressure of hydrogen of 10 mbar above atmospheric and a blower-stirrer stirring speed of 2,000 $min^{-1}$.

The experimentally determined activity values for the catalysts prepared according to the examples and comparison examples are listed in Table 1.

TABLE 1

| Catalyst | Catalyst Activities | | Activity [ml/g.min] |
|---|---|---|---|
| | Activated Carbon | $H_2O_2$-wash | |
| Comparison Ex. 1 | Batch 1 | No | 35 |
| Example 1 | Batch 1 | Yes | 62 |
| Comparison Ex. 2 | Batch 2 | No | 82 |
| Example 2 | Batch 2 | Yes | 108 |

The catalyst reactivity in the case of activated carbon batch 1 was increased from 35 to 62 ml $H_2$/g.min and in the case of activated carbon batch 2 from 82 to 108 ml $H_2$/g.min, due to the oxidative pretreatment.

To explain these unexpected increases in activity, surface analysis of the catalysts was performed using XPS (X-ray photoelectron spectroscopy). It was found that activated carbon which had been washed with nitric acid had amine, ammonium and nitrite/nitrate groups due to the nitric acid wash in addition to the desired active C/O functional groups.

The surface concentration of these nitrogen-containing functional groups was reduced to below the limit of detection by XPS measurement of 0.1 area percentage points by oxidative pretreatment with hydrogen peroxide. As the examples show, this effect was achieved with a treatment time of only four hours.

Table 2 shows the results of XPS measurements on the activated carbon supports before and after washing with hydrogen peroxide and after impregnation with palladium. The surface concentrations of nitrogen were obtained by integrating the N1s signals.

In the case of supports or catalysts washed with hydrogen peroxide, the nitrogen concentrations at the surface were all below the detection limit of 0.1 area percentage points. The increases in activity which were found correlated well with the reduced surface concentration of nitrogen.

A further advantage of pretreating the nitric acid washed activated carbons with hydrogen peroxide is an additional reduction in surface contamination by traces of inorganic compounds.

If the activated carbon supports are not pretreated with hydrogen peroxide, impregnation with palladium leads to an increase in surface concentration of nitrogen due to flushing out the pores in the support. Also, the amount of trace contaminants on the surface which are partially removed by washing with $HNO_3$ such as e.g. Al, Si, Mg, Fe etc., which could be significant with respect to the acid/base properties of the catalyst surface, increase again in the case of non-$H_2O_2$-pretreated supports during impregnation with Pd.

In the case of pretreating supports which have been washed with nitric acid with hydrogen peroxide, this increase does not occur. Thus a purification effect by $H_2O_2$ was established, involving the removal of both nitrogen-functional surface groups and also other surface contaminants.

Very similar XPS peak intensities were measured for all the final Pd/C catalysts based on HNO$_3$/H$_2$O$_2$-conditioned support carbons, i.e. the surface concentration produced, or the dispersion of the noble metal, was much more constant. This was not the case with Pd/C catalysts which were prepared using support carbons washed only with HNO$_3$. Here, large batch-to-batch variations in Pd intensities were observed.

These tests show that XPS measurements are an appropriate means for checking the result of oxidative pretreatment with hydrogen peroxide.

TABLE 2

Surface concentration of nitrogen-containing functional groups

| Catalyst | Activated Carbon | H$_2$O$_2$-wash | Surface Concentration of Nitrogen (atom-percent) |
|---|---|---|---|
|  | Batch 1 | No | 0.18 |
|  | Batch 1 | Yes | —* |
|  | Batch 2 | No | 0.89 |
|  | Batch 2 | Yes | —* |
| Comparison Ex. 1 | Batch 1 | No | 0.73 |
| Example 1 | Batch 1 | Yes | —* |
| Comparison Ex. 2 | Batch 2 | No | 1.53 |
| Example 2 | Batch 2 | Yes | —* |

*below the limit of detection

We claim:

1. A process for preparing a hydrogenation catalyst having at least one catalytically active noble metal component selected from the group consisting of Pt, Pd, Rh, Ru, Os, and Ir and optionally at least one promotor or modifier on an activated carbon support washed with nitric acid, comprising subjecting said nitric acid washed activated carbon support to an oxidative pretreatment with an aqueous solution containing 0.1 to 30% by weight of an oxidizing agent, washing the resulting activated carbon support with water, and thereafter applying said catalytically active noble metal component and optionally said at least one promotor or modifier to said support.

2. The process according to claim 1, wherein the oxidizing agent is a source of hydrogen peroxide.

3. The process according to claim 2, wherein hydrogen peroxide is used.

4. The process according to claim 1, wherein said activated carbon is a finely divided form with an average particle diameter of 15 to 30 μm.

5. The process according to claim 1, wherein said activated carbon is a molded shape of a dimension of 1 to 5 mm.

6. The process according to claim 1, wherein said activated carbon has an ash content of less than 2% by weight.

7. The process according to claim 1, further comprising subjecting said support containing said catalytically active component to a reducing agent.

* * * * *